(12) United States Patent
Haeusler

(10) Patent No.: US 8,224,066 B2
(45) Date of Patent: Jul. 17, 2012

(54) METHOD AND MICROSCOPY DEVICE FOR THE DEFLECTOMETRIC DETECTION OF LOCAL GRADIENTS AND THE THREE-DIMENSIONAL SHAPE OF AN OBJECT

(76) Inventor: Gerd Haeusler, Erlangen (DE)

( * ) Notice: Subject to any disclaimer, the term of this patent is extended or adjusted under 35 U.S.C. 154(b) by 751 days.

(21) Appl. No.: 12/119,890

(22) Filed: May 13, 2008

(65) Prior Publication Data

US 2008/0317334 A1    Dec. 25, 2008

Related U.S. Application Data

(60) Provisional application No. 60/932,181, filed on May 29, 2007.

(51) Int. Cl.
*G06K 9/00* (2006.01)
(52) U.S. Cl. ........................................................ 382/154
(58) Field of Classification Search .................... 382/154
See application file for complete search history.

(56) References Cited

U.S. PATENT DOCUMENTS

| | | | |
|---|---|---|---|
| 4,141,032 A | | 2/1979 | Haeusler |
| 5,847,832 A * | 12/1998 | Liskow et al. ................. | 356/613 |
| 6,940,609 B2 * | 9/2005 | Scheiner ......................... | 356/605 |
| 6,956,963 B2 * | 10/2005 | Ulrich et al. .................... | 382/154 |
| 7,009,718 B2 * | 3/2006 | Fujita .............................. | 356/604 |
| 7,327,473 B2 * | 2/2008 | Harding et al. ................. | 356/600 |
| 7,738,695 B2 * | 6/2010 | Shorte et al. ................... | 382/154 |

FOREIGN PATENT DOCUMENTS

DE    2655525 C3    5/1979

(Continued)

OTHER PUBLICATIONS

Gerd Häusler, et al., Microscopic phase-measuring deflectometry, Optical Society of America, May 25, 2007, pp. 1-4, Institute of Optics, Information and Photonics, Max-Planck—Research Group, University of Erlangen-Nuremberg, Staudtstr. 7/B2, 91058 Erlangen, Germany.

(Continued)

*Primary Examiner* — Jingge Wu
(74) *Attorney, Agent, or Firm* — Laurence A. Greenberg; Werner H. Stemer; Ralph E. Locher

(57) ABSTRACT

The invention relates to a method and an apparatus for high-resolution deflectometric determination of the local slope and of the three-dimensional shape of an object (6). The apparatus comprises a microscopic imaging system (5, 4, 8) having a numerical aperture (sin u), a focus plane (6a) and a receiving unit (9, 10); an illuminating system (1, 3, 4, 13, 13a) having a grating generator (1) that preferably generates a sine grating (2); and a control and evaluating unit. The object (6) is located in the object space of the imaging system. The illuminating system (13, 13a), which is fashioned as an illuminating system for reflected-light objects or for transmitted-light objects, generates a series of grating images (7), which are projected as virtual images into the object space a distance d from the focus plane of the microscopic imaging system. The imaging system images onto a receiving unit, as a modulated image, the object and simultaneously the grating image reflected in the object or the transmitted grating image. The local slope components of the object surface are determined from the series of modulated images with the aid of the evaluating unit.

14 Claims, 4 Drawing Sheets

FOREIGN PATENT DOCUMENTS

DE  19944354 A1  4/2001

OTHER PUBLICATIONS

Engelhardt et al., "Acquisition of 3-D data by focus sensing", Applied Optics, vol. 27, No. 22, Nov. 15, 1988 pp. 4684 to 4689.

Haeusler et al., "Microdeflectometry—a novel tool to acquire 3D microtopography with nanometer height resolution", Institute of Optics, Information and Photonics, Max Planck Research Group, University of Erlangen-Nurenberg, Erlangen, Germany, compiled Feb. 15, 2008, pp. 1-3.

Haeusler et al., "Photography with increased depth of field", Zeiss Inform., Oberkochen, vol. 29, 1986, Heft 98, pp. 9-13.

* cited by examiner

METHOD AND MICROSCOPY DEVICE FOR THE DEFLECTOMETRIC DETECTION OF LOCAL GRADIENTS AND THE THREE-DIMENSIONAL SHAPE OF AN OBJECT

The present application claims the priority of Provisional Application 60/932,181 of May 29, 2007, which is hereby incorporated by reference into the present application.

BACKGROUND OF THE INVENTION

Field of the Invention

For measuring bright free-form surfaces such as for example automobile windows, painted body work, aspherical lenses, polished plumbing fixtures and so forth, deflectometric methods have been known for some years, as described for example in the inventor's earlier German Patent DE 199 44 354. As described by way of example in FIG. 1, macroscopic deflectometric methods essentially comprise a diffusely radiating grating, the specimen and an observing and evaluating apparatus. The observing apparatus, a camera in FIG. 1, images the specimen and simultaneously acquires the distorted mirror image of the grating reflected via the surface of the specimen. The local gradient of the specimen surface is determined from this distortion. The prerequisite is that the grating be disposed at a distance d from the specimen, and thus not projected onto the test object as in the case of so-called fringe projection for the three-dimensional measurement of diffusely scattering objects.

What is commonly used as a grating is a screen in the form of a matte disk, onto which a sinusoidal pattern is projected as a "grating," or also a screen in the form of an LCD monitor that displays a sine pattern. A sine pattern in the form of a transparency, for example as a slide or a photolithographically produced mask, is also suitable, but in general there is required a diffuser that ensures that light is incident on the small pupil of the imaging camera. Both components of the surface slope in the x and y directions are measured with the aid of gratings that are oriented in two distinct directions. Because the grating is large and light is emitted diffusely in all directions, it is possible to measure even more strongly curved specimens because light always reaches the pupil of the imaging optics. For the sake of completeness it should be mentioned that the method can also be modified in simple fashion for measurements in transparency, for example in order to inspect the distortions of automobile windows in through vision.

The above-described method is suitable for macroscopic applications where the observation-side aperture is very small, for example roughly in the range of 1:100. It is not, however, suitable for microscopic applications in which it is desired to have larger observing apertures and a spatial resolution in the range of some micrometers or less. There are profound physical reasons for this; one important reason is that in microscopic applications, because of the short back-focus distances and because illumination and observation are coaxial, there is no room for a physical "screen" between specimen and observing optics. Further, a diffuser cannot be inserted into a coaxial incident-light setup without disrupting the imaging. A further fundamental reason that there has not yet been a deflectometric microscope is that the large imaging aperture required when the required resolution is high poses problems: The depth of focus, which can easily be in the range of 100 mm or more in macroscopic deflectometry, is usually significantly less than 1 mm in microscopic imaging, and goes down to the submicrometer range.

Deflectometry can, however, find broad application for microscopic objects and for surface inspection on such objects, for example on finely machined surfaces such as seals, injection nozzles, also in the inspection of wafers or other electronic components; equally for the inspection of impressions made by firing pins in cartridge casings. Some applications of microdeflectometry and the functional principle are described in the publication by G. Häusler, M. Knauer and C. Richter, Optics Letters, Vol. 33, Issue 4, pp. 396-398 (2008). Deflectometry yields images that reproduce the local slope (gradient) of the surface shape. The working distance plays no role because of optical differentiation with respect to position, and long-wavelength variations of the surface shape lead to weak signals. Deflectometry is extremely sensitive to short-wavelength local surface defects such as occur in the case of surface flaws. In principle, however, the overall surface shape can also be determined from the measured data by integration.

Methods that give, at least approximately, the first derivative of a height or phase distribution (including in transparency) are also known in microscopy. The most important is differential interference contrast. Here an interference apparatus employing polarization optics creates a dual image of the specimen, one image being displaced laterally by a distance $\Delta x$ relative to the other image. If $\Delta x$ is of the order of the lateral resolution of the observing optics and the phase difference between the two images is $\pi$, then what is observed is approximately the derivative of the local phase of the transmitted or reflected light in one direction. Unfortunately, the differential interference contrast cannot be quantitatively interpreted, or at any rate not in simple fashion. What is more, the sensitivity is slight unless complicated phase-measuring methods are employed. The dynamics of the measurement, that is, the range of the slope that can be reproduced, is also slight. Further, the coherence and the quality of the optics must meet strict standards because the method is an interferometric one. Finally, the method yields only one component of the gradient.

DETAILED DESCRIPTION OF THE INVENTION

Figure 1:
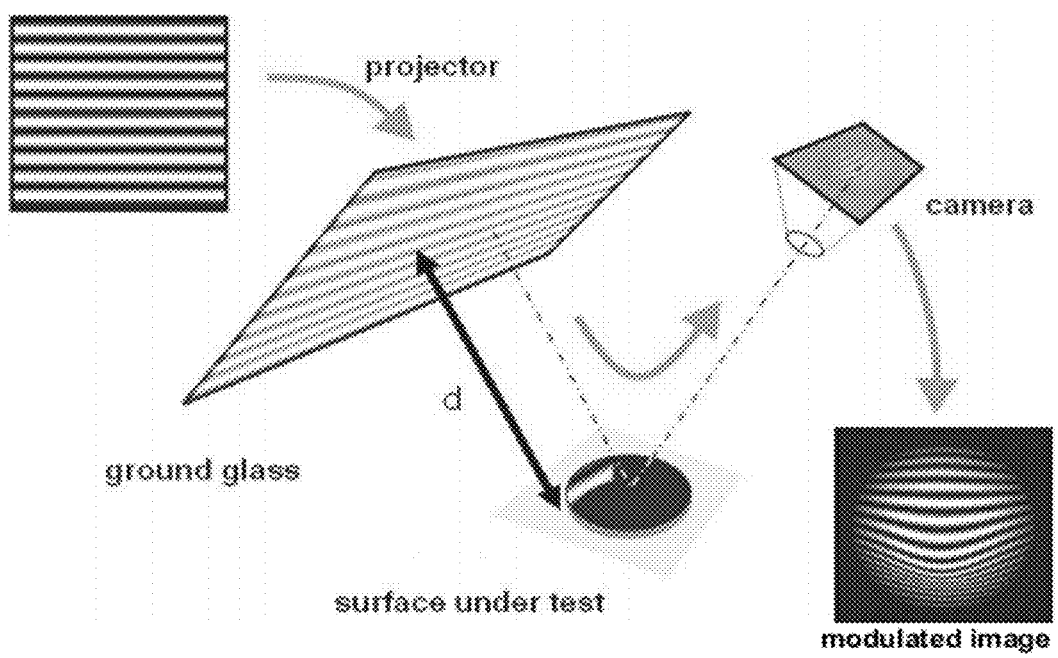
FIG. 1 is a schematic illustration of macroscopic deflectometry according to the above-described prior art.
Figure 2:
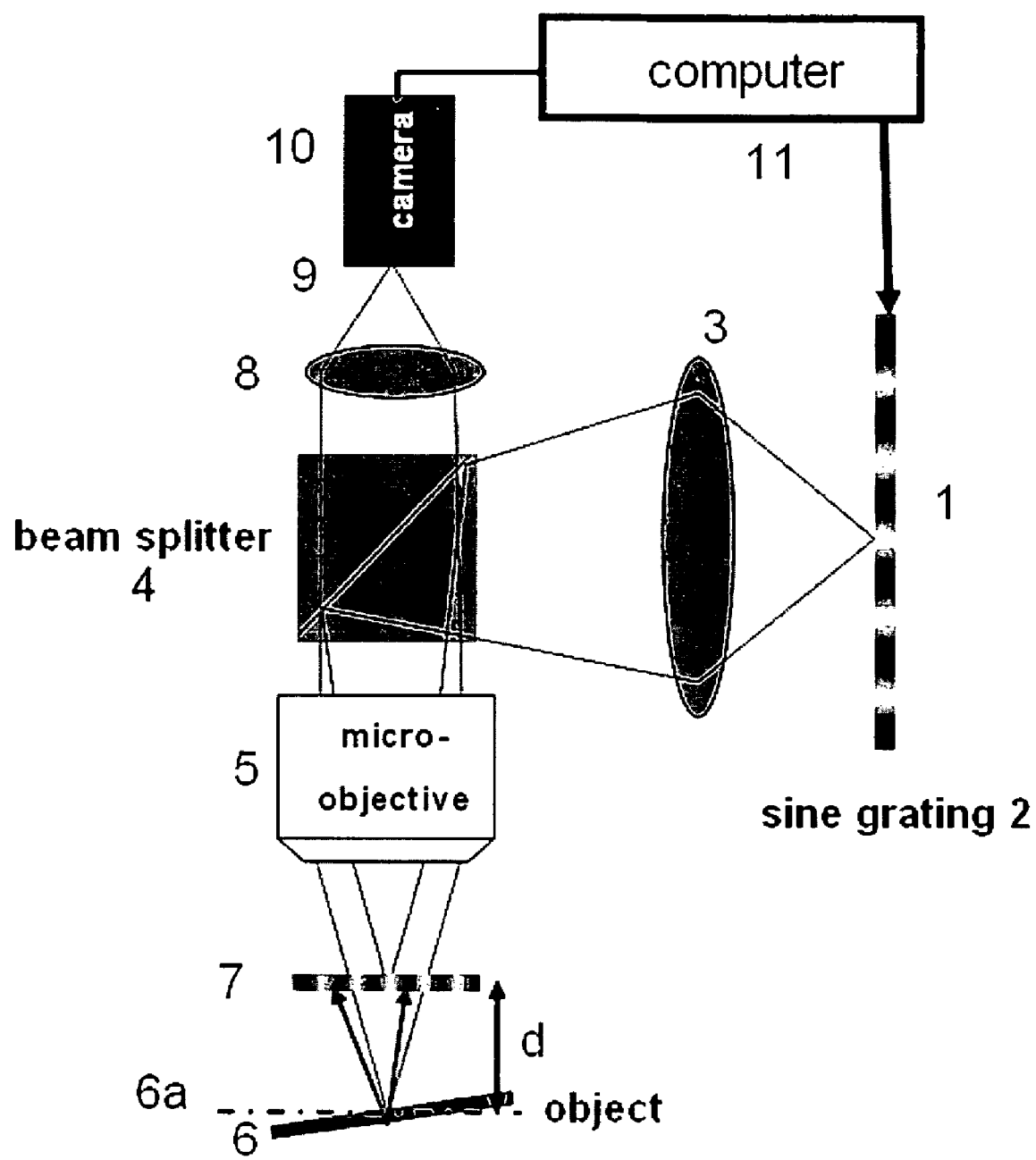
FIG. 2 is a schematic illustration of the microscopic-domain deflectometry application according to the invention.

The above-mentioned disadvantages of the prior art are to be remedied according to the invention. The method described in the inventor's above-mentioned German Patent DE 19944354 is modified according to the invention in such fashion as described in FIG. 2. Here FIG. 2 depicts only one exemplary embodiment. Modifications of the principle are described in what follows. A controllable grating generator 1, for example an LCD screen, or a micromirror array is so controlled that a sine grating 2 is represented. This grating is imaged by illuminating optics 3 via a beam splitter 4 and micro-objective 5 in the vicinity of specimen 6. The distance between grating image 7 and specimen 6 is d. Here it is essential that the grating image is a virtual image and is not projected onto a diffuser. If the grating is not generated by or on a diffusely scattering screen by the grating generator, as in the case of the LCD, but instead takes the form for example of a transparent mask, then the grating in object space should be imaged via Köhler illumination set up in conventional fashion.

Micro-objective 5 images specimen 6, via auxiliary optics 8 if appropriate, in image plane 9 of a camera 10 and is stored with the aid of a computer 11. The computer can serve simultaneously for storing the images and for controlling the grating generator and the camera. The image acquired also contains an (indistinct) mirror image of the grating that is reflected on the specimen. This is also possible if the object is not planar but also displays sloping surface elements because, indeed, the large observing aperture and the large illuminating aperture of the microscopic system assist. It should be remembered that the diffuser is necessary for macroscopic deflectometry because the imaging aperture is small.

The local phase in the image of the reflected grating depends on the slope at the specimen position (x,y) currently being examined, as well as on the grating period p and the distance d. This phase can be determined by known phase-shift methods such as Bruning's method, for example by acquiring a series of four grating images, the phase of the grating as presented being varied by 90° each time. From such a series of images the phase can be determined, ordinarily to a precision of $1/1000$ of the grating period. With noise reduction, for example through prolonged exposure time, the precision can even be increased significantly. This phase is compared with the phase obtained when the specimen is replaced by a planar mirror. The phase difference at each image point is roughly proportional to the local slope of the specimen at this image point. In order to determine the two slope components in the x and y directions (components of the gradient), the grating is disposed once so that the grating lines run vertically to the x axis and once so that the grating lines run horizontally to the x axis. A grating that simultaneously contains two orthogonal grating directions is also possible. From the measured phase difference φ, the grating period p and the distance d, the local slope components $\alpha_x$ (e.g., in the x direction) can then be determined approximately as $$\alpha_x \sim \phi p / 2\pi d \quad (1)$$

or, depending on the optics (sine condition), from the arctangent or the arcsine of this quantity. Here account is taken of the fact that, because of the slope of the object, rays pass through only part of the pupil of the observing system when imaging takes place. Incidentally, the sensitivity according to equation (1) for microscopic deflectometry is only half as great as for macroscopic deflectometry. Diffraction at the object plays a greater role for very finely textured objects, so that the factor of proportionality can then be a different one, which must be worked out by calibration. An analogous procedure with the grating rotated through 90° is employed for the other slope component perpendicular to the x direction.

Figure 3:
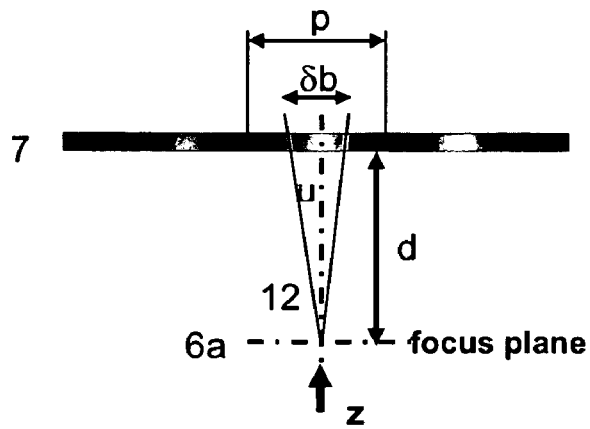
FIG. 3 is a diagram showing how the period of the grating image is usefully adapted to the distance d.

According to the invention, as FIG. 3 illustrates, the grating period is so adapted to the distance d and the observing aperture sin u that when the grating is indistinctly imaged, the geometrical indistinctness of the circle of confusion δb, which can be calculated in simple fashion from the numerical aperture of the micro-objective and d with the aid of aperture cone 12, is roughly one-half the period p of grating image 7.

A smaller grating period would degrade the contrast of the grating image in focus plane 9 and thus the accuracy of phase determination. A larger grating period would decrease the sensitivity of the method.

The indistinctness product between the laterally resolvable distance δx on the object, which is given by the numerical aperture of the micro-objective, and the uncertainty δα of the slope measurement, is a minimum in the case of optimal adaptation of the grating period. It is described approximately by $$\delta x \delta \alpha \sim \lambda Q. \quad (2)$$

Here λ is the wavelength of the light used and Q is a figure of merit given substantially by the noise of the system. Because the method is largely incoherent, Q is governed primarily by electronic noise and quantization noise. In practice Q values of around 500 or greater can be achieved with short exposure times. If special noise-reduction practices such as longer exposure time are employed, much higher Q values can be obtained.

It must be mentioned that deflectometry basically works only for reflective objects. In the case of high lateral resolution, however, as is found in microscopy with high numerical observing aperture, nearly all objects reflect. This too is different from the case in macroscopic deflectometry. The reason is that objects are "reflective" when the height variation of the object within the resolution of the microscope is smaller than roughly λ/4. Optically diffusely scattering objects can, however, be rendered reflective by choosing a longer wavelength λ, that is, by using deep-red light or even infrared light. A further possibility, which figures especially in the case of micro-objectives having large numerical aperture, is to use almost grazing light incidence or very oblique light incidence for illumination and imaging. Incidentally, the method can be employed within limitations even with diffusely scattering objects, because the series of grating images varying in phase shift, such as are acquired for evaluation, also has the physical meaning that a different illumination situation holds for each of the images in the series.

Thus images are acquired in this way with illumination from various directions, which images also differ markedly in appearance. Defects can be very clearly identified simply by determining the difference between two such images or determining the contrast, for example with the above-described four-shift method.

Equation (2) indirectly describes the attainable performance data for microdeflectometry: The product δxδα essentially describes the attainable uncertainty δh in height measurement (after integration) or also the sensitivity with respect to a change of height within the laterally resolvable distance δx. For a wavelength of λ=500 nm, a δh of roughly 1 nm is obtained. This is a remarkably small uncertainty of height measurement, such as is attained only by very high-quality interferometers. In deflectometry as described here according to the invention, however, the method is not an interferometric one. It therefore does not pose the usual problems of interferometry. Deflectometry can work with a very large illuminating aperture. At a large illuminating aperture there is scarcely any coherent noise or defocusing noise: The quality of the images generated is high, as can be inferred from images that were acquired with the scanning electron microscope. The method is not sensitive to vibrations; it can be employed for objects having high slope dynamics and can work with white light. The sensitivity can readily be increased to the range of δh~0.1 nm. A maximum measurable slope of more than +/−60° can be attained with a large numerical aperture. In macroscopic deflectometry such angle dynamics can be achieved only with giant matte disks and restrictions in terms of accuracy.

The distance d is freely selectable within wide limits: If d is chosen in the range of the Rayleigh depth of focus, a very small grating period can be chosen because the specimen and grating image 7 are imaged with practically no depth-of-focus problem. In this case the grating period is chosen as small as possible, say at the resolution limit of the micro-objective. This version of the method is disadvantageous, however, if the object is highly nonplanar, because d varies greatly from one object point to another. For such objects, and also because of the greater sensitivity for slope measurement, it is recommended that the grating distance d be chosen larger, even for example with a grating period just as large as the field of view of the micro-objective. Even larger distances d are possible, however, provided the grating period is appropriately adapted. A large distance d here has the advantage that the relative variation of the distance from each object point to the grating remains small, even for nonplanar objects, and thus the system can be calibrated more easily.

The system must be calibrated for quantitative measurement of the local object slope. To this end it is expedient to determine the distance d from grating image 7 to the focus plane of the micro-objective, and likewise the grating period. This can be done either computationally from the known geometrical data of the system or by acquiring suitable test objects. Further, the distortion of the grating image and of the specimen by the optics must be determined. Photogrammetry offers suitable aids for this purpose. One very simple option for calibration is to present a known, measured test object and with it determine the properties of the microdeflectometric system.

An extension and new property of the method is achieved according to the invention by an additional expansion of the depth of focus. In this way it becomes possible for the first time to obtain images such as otherwise can be acquired only with the scanning electron microscope, and even to do so in quantitative and three-dimensional fashion.

Scanning electron micrographs are distinguished by three properties: First, a slope-encoded representation of the object is obtained. Second, the lateral resolution is high (for many applications, however, it is not better than that of an optical microscope); third, the depth of focus is very great. The first two properties can already be achieved with the above-described microdeflectometry, and images of high quality and great vividness (slope-encoded) can be obtained. What is more, these images are quantitative, that is, the slope is locally measurable to high accuracy, and after integration the shape is also known.

If, however, the object has a height variation greater than the Rayleigh depth of focus, the lateral resolution decreases for the object regions that do not lie within the depth of focus of imaging. To be sure, this is not so salient as in the case of standard microscopy. In this sense microdeflectometry is more tolerant in terms of depth-of-focus problems. But an expansion of the depth of focus is nevertheless necessary for nonplanar objects. The solution according to the invention is now described.

Figure 5:
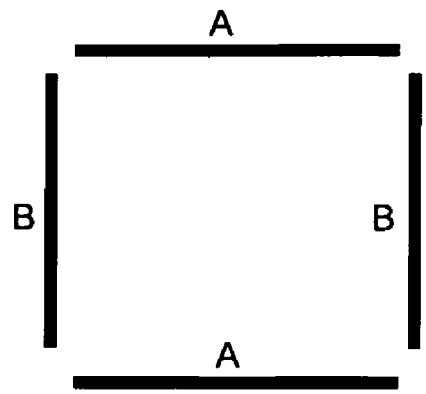
FIG. 5 is a diagrammatic illustration of an observing pupil having two pairs of slits.

A variety of methods are known for expanding the depth of focus in microscopic imaging. The simplest methods work with an annular pupil in the optical imaging of the specimen. An increased depth of focus is achieved in this way, as is generally known. The contrast decreases at higher frequencies, however, and there is a loss of light. It is also possible to insert a suitable phase plate into the pupil, which in known fashion introduces artificial aberrations that also entail an expansion of the depth of focus. It is also known that spherical aberration expands the depth of focus. Instead of an annular pupil, a pupil having four slits disposed to form the sides of a square, as depicted in FIG. 5, can also be introduced. The anisotropy of this pupil has the advantage that the grating lines in the horizontal direction and in the vertical direction are imaged better than with the annular pupil. The slit spacing in this pupil is so chosen that the optical transfer function of the imaging system passes the grating period p with optimal contrast.

Figure 4:
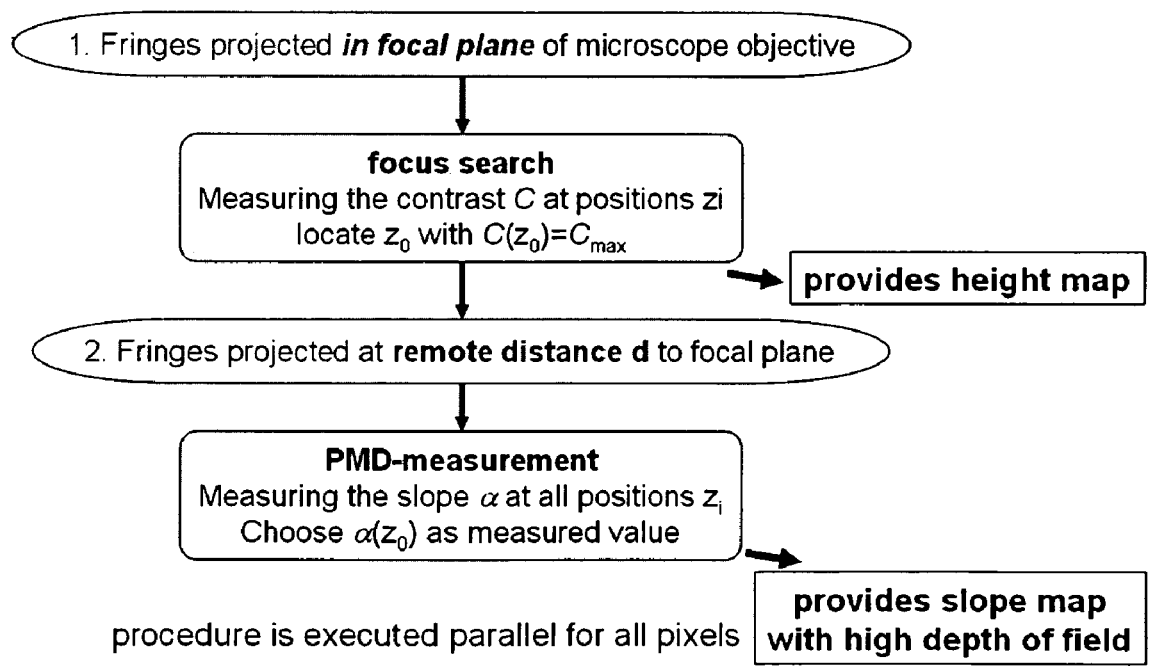
FIG. 4 is a flow chart for deflectometry with expanded depth of focus.

A further option for achieving an expansion of the depth of focus without special hardware or interventions in the pupil is the following: As described above, slope images of the specimen are acquired. Now, however, a series of slope images are acquired for distinct positions $z_i$ of the specimen along the optical axis of the micro-objective. To this end the object is translated along the optical (z) axis with the aid of a translating apparatus, for example a mechanical sled or a piezodrive. In this way every position of the specimen is acquired at least once in the best plane of sharpness. From the series of slope images, each with sharp and indistinct object details, images having great depth of focus are computed as is known from the inventor's German Patent 2655525 (1976) and U.S. Pat. No. 4,141,032 (1979) or from the article by G. Häusler and E. Körner, "Imaging with Expanded Depth of Focus," Zeiss Information No. 98, Vol. 29 (1986), 9-13, Oberkochen. In order to identify the sharp object details in each case, according to the invention, the grating can be projected into focus plane 6a of microscope objective 5 (i.e., d is chosen equal to zero) and the series of images can be acquired in similar fashion to what was described above for determining the slope, in each case for various positions $z_i$ of the specimen along the optical axis of the micro-objective. FIG. 4 reproduces the scheme for one pixel. The method, however, runs in parallel for all positions (x,y) on the specimen.

The principle is based on the method of "acquisition of 3-D data by focus sensing," described by K. Engelhardt and G. Häusler in Appl. Opt. 27 (1988), 4684-4689, where again a grating is imaged onto the object and a focus series is acquired. There, however, in contrast to the method according to the invention, the contrast is not determined at each focus position $z_i$; instead, only the intensity I(z) of each image point along the z axis is determined. From the intensity function I(z), the position of best focusing is determined by inverting the contrast with strong defocusing. This method is significantly less accurate and not purely local; that is, it requires nearness relations of the points. On the other hand, contrast determination at each z position by phase-shift methods, as is proposed for focus searching according to the invention, is local and very accurate.

For each position $z_i$ of the specimen, as in slope measurement, a series of images with the grating phase-shifted is thus acquired. The contrast of the grating image in each camera pixel can be determined separately from these phase-shifted images. This contrast is stored in a computer for each camera pixel and each position of the specimen along the optical axis. Now, from the series $C(z_i)$ of contrast data, it is possible to determine which position on the specimen (which camera pixel) was exactly in focus at which position of the specimen along the optical axis; this is done by determining for each camera pixel that position along the optical axis where the contrast exactly displays a maximum. In practice the known four-shift algorithm has proved suitable for determining the contrast C; that is, four images $I_1, I_2, I_3, I_4$ with phase shifts of respectively 0°, 90°, 180°, 270° are acquired for each position $z_i$ of the specimen along the optical axis of the micro-objective. In this case the contrast C is calculated as $$C^2=4[(I_1-I_3)^2+(I_2-I_4)^2]/(I_1+I_2+I_3+I_4)^2. \quad (3)$$

Higher accuracies can be obtained with multi-shift methods if this is necessary. It should be noted that the sampling distance of the focus series with the various specimen positions along the optical axis is so chosen that at least three positions are traversed within the contrast curve C(z) of optical imaging. The contrast curve can then be interpolated and the position z of best focus for each pixel can be determined to an accuracy of a few nanometers. In this way a highly accurate height map z(x,y) of the specimen can be obtained. Denser sampling along the optical axis increases the accuracy of the height map but also requires more time. If a larger grating period p is chosen, C(z) becomes broader and the sampling distance of the focus series can be chosen larger. This is expedient for objects having great depth because it saves time. As described above, the slope from the deflectometric data can be additionally inserted at each pixel of this height map. In this way it becomes possible for the first time to generate, by optical means, images as with the scanning electron microscope. What is novel, however, is that these images display quantitative slope encoding, great depth of focus and the three-dimensional shape as well as, in addition, very high angle dynamics. With an uncertainty of angle measurement in the range of a few seconds of arc and a maximum slope of the surface element equal to the aperture of the micro-objective—which can be achieved in simple fashion—angle dynamics in the range significantly greater than 1000:1 can be achieved.

If the results are plotted as a two-dimensional intensity image, the measured slope at each image point will be encoded as an intensity or color, so that a high-quality image resembling those acquired with the scanning electron microscope are obtained. Further, the height map obtained can be given a pseudo-three-dimensional representation with the aid of a CAD program and, likewise, the measured slope (one component or also a transformed quantity such as curvature) at each image point can be additionally represented by grayscale encoding or color encoding. Thus one has a three-dimensional representation that can be rotated on the screen and through which height sections and so forth can also be made. If the slope data are not utilized, the method degenerates to pure shape measurement.

Because the illumination is largely spatially and temporally incoherent, the method is not susceptible to optical (coherent) noise and likewise not sensitive to vibrations. Thus it offers important advantages over interferometry.

Figure 6:
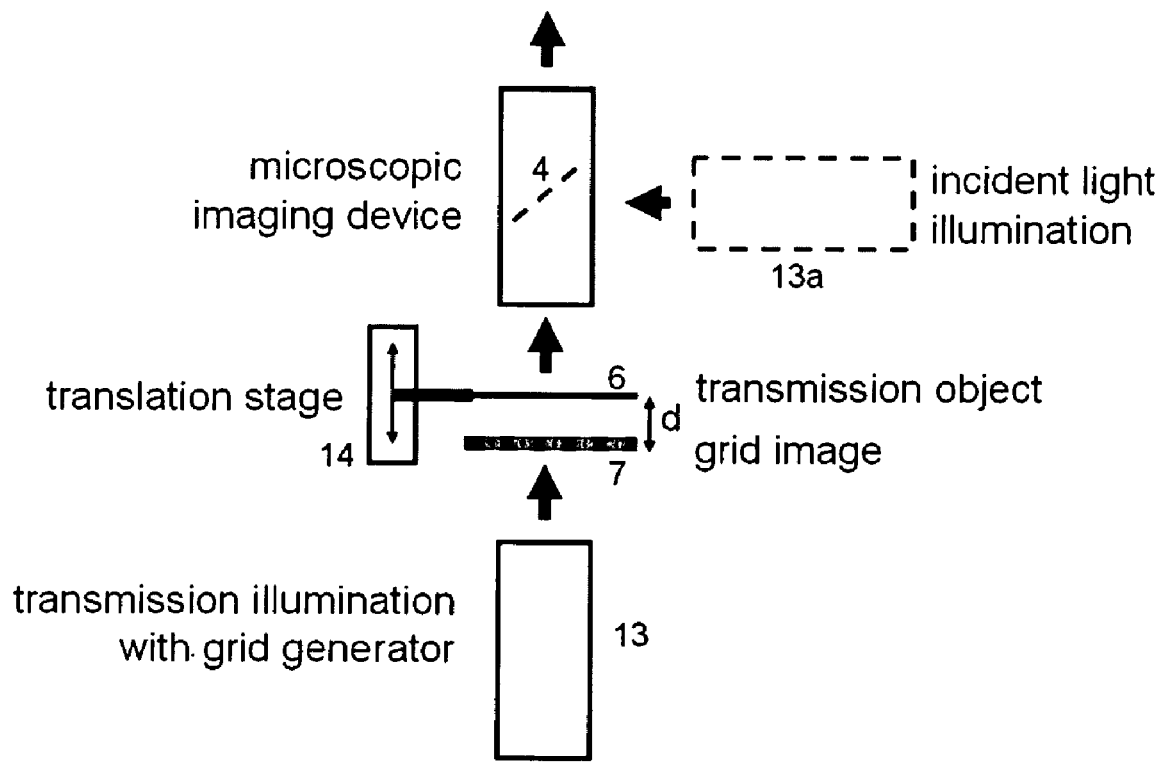
FIG. 6 is a schematic illustration of microdeflectometry according to the invention with illumination of the object in transmission (transmission object).

It must be mentioned that the method sketched in FIG. 2 is drawn for reflected-light microscopy. A completely analogous method can be described for transmitted-light microscopy. Here the grating is not—as drawn in FIG. 2—"reflected" by a beam splitter 4 from above into the vicinity of the specimen; instead, as in a transmitted-light microscope, grating image 6 is introduced in conventional fashion "from below" with an illuminating apparatus 13, as sketched in FIG. 6. Transmitted-light objects can be measured with this configuration; that is, for example, the gradient of the local phase distribution, for example within a cell, or also local refractive-index distributions in technical objects can be measured. Naturally, the conventional modifications with polarizing optics can also be employed: For example, illumination can be effected with two successive crossed polarizations and the birefringence of the phase gradient can be determined. It is even possible to determine the optical thickness for each position (x,y) by spatial integration. In principle, naturally, the microscopic configuration can contain both illuminations, in reflected light and in transmitted light, each being turned on and off as chosen.

A technically simple implementation of microdeflectometry relates to generating the grating. It is not categorically necessary to generate a sine grating, because the grating is imaged indistinctly. In principle, a rectangular (Ronchi) grating might also be sufficient, but then the harmonic frequencies will lead to wavelike artifacts. Nevertheless, this easily implemented technique is an option for microdeflectometry.

A further option for implementing sine fringes is to employ Fourier optics. A sine grating is easily generated in this way by a double slit in the pupil of the optics that generates grating image 7. In FIG. 2 it is expedient not to use exclusively the micro-objective for this purpose but instead a supplemental optics such as is symbolized by lens 3 in FIG. 2. Screen 1 with sine grating 2 then falls away and there is merely an illuminating optics analogous to a standard microscope but with the double slit in the condenser pupil. Instead of a double slit, which restricts the illuminating aperture, a biprism can also be inserted in the pupil of the illuminating optics in such fashion that grating image 7 is generated by interference. This also works for a large illuminating aperture. Finally, interference can also be combined with polarization optics, and instead of the biprism a Wollaston prism with polarizers can be used to generate grating image 7, as in differential interference contrast. This method offers the option of using a conventional microscope with differential interference contrast modified for microdeflectometry.

The invention claimed is:

1. A method for high-resolution deflectometric measurement of a local slope and a three-dimensional shape of an object, the method which comprises:
    providing a microscopic imaging system having a numerical aperture, a focus plane, and a receiving unit; an illuminating system having a grating generator configured to generate a grating; and a control and evaluating unit;
    placing an object in an object space of the imaging system;
    with the illuminating system, generating a series of grating images in the object space at a distance d from a focus plane of the microscopic imaging system;
    controlling the illuminating system to image the grating images into the object space with an adjustable period p;
    choosing the period p in dependence on a distance d so large that a contrast of the observed modulated images is sufficient for low-noise evaluation;
    with the imaging system, imaging a modulated image onto a receiver unit, the modulated image being formed of the object and the grating image reflected at the object or transmitted through the object; and
    determining local slope components of the object surface from the series of modulated images with the evaluating unit.

2. The method according to claim 1, wherein the grating generator is configured to generate a sine grating.

3. The method according to claim 1, wherein the illuminating system is configured for illuminating reflected-light objects or transmitted-light objects.

4. The method according to claim 1, wherein the contrast sufficient for low-noise evaluation is achieved by so choosing the period p that a diameter δb of the circle of confusion due to the indistinct imaging of the grating image with the aperture cone at distance d is preferably equal to roughly one-half the period.

5. The method according to claim 1, which comprises combining the method with an expansion of a depth of focus for nonplanar objects.

6. A method for high-resolution deflectometric measurement of a local slope and a three-dimensional shape of an object, the method which comprises:
- providing a microscopic imaging system having a numerical aperture, a focus plane, and a receiving unit; an illuminating system having a grating generator configured to generate a grating; and a control and evaluating unit;
- placing an object in an object space of the imaging system;
- with the illuminating system, generating a series of grating images in the object space at a distance d from a focus plane of the microscopic imaging system;
- with the imaging system, imaging a modulated image onto a receiver unit, the modulated image being formed of the object and the grating image reflected at the object or transmitted through the object;
- determining local slope components of the object surface from the series of modulated images with the evaluating unit; and
- combining the method with an expansion of a depth of focus for nonplanar objects; and
- first determining a height map z(x,y) of the object;
- acquiring local slope components at various object positions $z_1, z_2, \ldots, z_N$, moving the object along the optical axis of the imaging system in steps to positions $z_1, z_2, \ldots, z_N$, so that each object point lies near the focus plane at least once; and
- associating with each point z(x,y) of the height map the local slope components measured at the height z, to thereby produce a slope image with depth of focus.

7. The method according to claim 5, which comprises:
- acquiring a height map by imaging the grating image in the focus plane at d=0;
- moving the object along the optical axis of the imaging system in steps to positions $z_1, z_2, \ldots, z_N$, so that each object point lies near the focus plane at least once;
- employing a phase-shift method to determine a grating image contrast C for all object positions $z_1, z_2, \ldots, z_N$ and at each image point;
- for each image point, determining a position z(x,y) having a maximum grating contrast by interpolation based on a behavior of the grating contrast; and
- wherein the respective position z(x,y) represents the shape of the object surface or height map.

8. The method according to claim 7, wherein the step length of the z positions $z_1, z_2, \ldots, z_N$ and the grating period p are so adapted that at least three positions $z_i, z_{i+1}, z_{i+2}$ lie within the half-value width of the contrast function C.

9. The method according to claim 7, wherein the slope data with depth of focus at each position x,y of the object surface are represented with intensity encoding in such fashion that there is produced a two-dimensional image similar to the images that are acquired with the scanning electron microscope.

10. The method according to claim 7, which comprises representing the height map in spatially pseudo-three-dimensional fashion and representing at each surface point z(x,y) the local slope with intensity encoding, to thereby produce a slope-encoded height map that can be rotated on the screen.

11. The method according to claim 1, wherein the illuminating apparatus with the grating imaging is disposed to measure objects in transmission.

12. A method for high-resolution deflectometric measurement of a local slope and a three-dimensional shape of an object, the method which comprises:
- providing a microscopic imaging system having a numerical aperture, a focus plane, and a receiving unit; an illuminating system having a grating generator configured to generate a grating; and a control and evaluating unit;
- placing an object in an object space of the imaging system;
- with the illuminating system, generating a series of grating images as virtual images in the object space at a distance d from a focus plane of the microscopic imaging system;
- controlling the illuminating system to image the grating images into the object space with an adjustable period p;
- with the imaging system, imaging a modulated image onto a receiver unit, the modulated image being formed of the object and the grating image reflected at the object or transmitted through the object;
- choosing the period p in dependence on a distance d so large that a contrast of the observed modulated images is sufficient for low-noise evaluation; and
- determining local slope components of the object surface from the series of modulated images with the evaluating unit.

13. The method according to claim 12, wherein the contrast sufficient for low-noise evaluation is achieved by so choosing the period p that a diameter δb of a circle of confusion due to the indistinct imaging of the grating image with the aperture cone at distance d is preferably equal to roughly one-half the period.

14. The method according to claim 1, which comprises placing the grating generated by the grating generator outside of a path of imaging rays of the microscopic imaging system.

* * * * *